United States Patent
Cohen et al.

(10) Patent No.: US 9,494,605 B2
(45) Date of Patent: Nov. 15, 2016

(54) DIAGNOSTIC TOOLS FOR CHARCOT-MARIE-TOOTH DISEASE

(75) Inventors: Daniel Cohen, Le Vésinet (FR); Ilya Chumakov, Vaux le Penil (FR); Oxana Guerassimenko, Milly-la-Foret (FR); Serguei Nabirochkin, Chatenay Malabry (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 13/510,700

(22) PCT Filed: Nov. 19, 2010
(Under 37 CFR 1.47)

(86) PCT No.: PCT/EP2010/067855
§ 371 (c)(1),
(2), (4) Date: Dec. 5, 2012

(87) PCT Pub. No.: WO2011/061304
PCT Pub. Date: May 26, 2011

(65) Prior Publication Data
US 2013/0217036 A1  Aug. 22, 2013

(30) Foreign Application Priority Data
Nov. 20, 2009  (EP) .................................. 09306121

(51) Int. Cl.
| | |
|---|---|
| *G01N 33/92* | (2006.01) |
| *G01N 33/50* | (2006.01) |
| *G01N 33/88* | (2006.01) |
| *G01N 33/74* | (2006.01) |
| *G01N 33/78* | (2006.01) |
| *G01N 33/94* | (2006.01) |
| *G01N 33/68* | (2006.01) |

(52) U.S. Cl.
CPC .............. *G01N 33/92* (2013.01); *G01N 33/50* (2013.01); *G01N 33/6896* (2013.01); *G01N 33/88* (2013.01); *G01N 33/6812* (2013.01); *G01N 33/743* (2013.01); *G01N 33/78* (2013.01); *G01N 33/942* (2013.01); *G01N 33/9433* (2013.01); *G01N 2800/285* (2013.01)

(58) Field of Classification Search
None
See application file for complete search history.

(56) References Cited

U.S. PATENT DOCUMENTS

| | | | | |
|---|---|---|---|---|
| 4,186,251 | A * | 1/1980 | Tarbutton ........................ | 435/11 |
| 4,366,143 | A * | 12/1982 | Midgley .............. | G01N 33/743 436/501 |
| 7,060,452 | B2 * | 6/2006 | Rothblat et al. ................ | 435/11 |
| 2005/0004004 | A1 * | 1/2005 | Bellotti ................ | A61K 9/1275 530/359 |
| 2008/0057509 | A1 | 3/2008 | Lupski et al. | |
| 2008/0171080 | A1 * | 7/2008 | Schaebitz et al. ............ | 424/450 |
| 2009/0170072 | A1 * | 7/2009 | Mink et al. ........................ | 435/5 |

FOREIGN PATENT DOCUMENTS

| | | | |
|---|---|---|---|
| GB | 1429525 | 3/1976 | |
| JP | 2005-314256 | 11/2005 | |
| KR | 10-2007-0062480 | 6/2007 | |
| WO | WO 92/21694 | 12/1992 | |
| WO | WO 9221694 A1 * | 12/1992 | ............. C07H 21/00 |
| WO | WO 2007094027 A2 * | 8/2007 | ............. G01N 33/50 |
| WO | WO 2009068668 A1 * | 6/2009 | |

OTHER PUBLICATIONS

Yao et al., Lipid abnormalities in hereditary neuropathy. Part 4. Endoneurial and Liver Lipids of HMSN-III (Dejerine-Sottas disease), J. Nerol. Sci. 1981, Nov.-Dec. 52(2-3): 179-190.*
McLeod, Investigation of peripheral neuropathy, Journal of Neurology, Neurosurgery, and Psychiatry 1995, 58:274-283.*
Giambonini-Brugnoli et al., Distinct disease mechanisms in peripheral neuropathies due to altered peripheral myelin protein 22 gene dosage or a Pmp22 point mutation, Neurobiology of Disease 18 (2005) 656-668.*
Dong et al., Jones oxidation and high performance liquid chromatographic analysis of cholesterol in biological samples, Journal of Chromatography B, 858 (2007) 239-246 at abstract, 239-241.*
Conrads, T. P. et al. "Sampling and analytical strategies for biomarker discovery using mass spectrometry" *BioTechniques*, Jun. 2006, pp. 799-805, vol. 40.
Patroclo, C. B. et al. "Autosomal Dominant HMSN with Proximal Involvement" *Arquivos De Neuro-Psiquiatria*, 2009, pp. 892-896, vol. 67, No. 3B.
Yao, J. K. et al. "Lipid Abnormalities in Hereditary Neuropathy" *Journal of the Neurological Sciences*, 1978, pp. 225-236, vol. 36.
Niebroj,-Dobosz, I. et al. "Serum lipids in some polyneuropathies" *Neurologia I Neurochirurgia Polska*, 1977, pp. 421-426, vol. 27, No. 4.
Swartz, G. et al. "Antibodies to cholesterol" *Proceedings of the National Academy of Sciences USA*, Mar. 1988, pp. 1902-1906, vol. 85.
XP007912053, "Charcot-Marie-Tooth Disease" pp. 1-8, retrieved from the internet: http://en.wikipedia.org/wiki/charcot-Marie-tooth_disease>, retrieved on Mar. 4, 2010.

* cited by examiner

*Primary Examiner* — Andrea S Grossman
(74) *Attorney, Agent, or Firm* — Saliwanchik, Lloyd & Eisenschenk

(57) ABSTRACT

The present invention relates in particular to methods of detecting predisposition to or diagnosis and/or prognosis of Charcot-Marie-Tooth (CMT) and related disorders. More specifically, the invention relates to development, validation and application of new biomarkers, which can be used for detecting the presence or risk of CMT disease and related disorders. In particular, the present invention relates to metabolite, lipid, carbohydrate and proteinaceous biomarkers that can be measured in biological body fluids and easily available extracts of biopsies, which can be used to aid in the detection, prediction of drug treatment and follow up of this treatment of neurodegenerative disorders, including CMT disease. The present invention also relates to methods for identification of CMT disease subtypes, assessing the responsiveness to the treatments and the efficacy of treatments in subjects having CMT or a related disorder.

5 Claims, No Drawings

DIAGNOSTIC TOOLS FOR CHARCOT-MARIE-TOOTH DISEASE

CROSS-REFERENCE TO RELATED APPLICATION

This application is the U.S. national stage application of International Patent Application No. PCT/EP2010/067855, filed Nov. 19, 2010, the disclosure of which is hereby incorporated by reference in its entireties, including all figures, tables and amino acid or nucleic acid sequences.

The present invention relates generally to the field of medicine. The present invention relates in particular to methods of detecting predisposition to or diagnosis and/or prognosis of Charcot-Marie-Tooth (CMT) and related disorders. More specifically, the invention relates to development, validation and application of new biomarkers, which can be used for detecting the presence or risk of CMT disease and related disorders. In particular, the present invention relates to metabolite, lipid, carbohydrate and proteinaceous biomarkers that can be measured in biological body fluids and easily available extracts of biopsies, which can be used to aid in the detection, prediction of drug treatment and follow up of this treatment of neurodegenerative disorders, including CMT disease. The present invention also relates to methods for identification of CMT disease sub-types, assessing the responsiveness to the treatments and the efficacy of treatments in subjects having CMT or a related disorder.

Charcot-Marie-Tooth disease ("CMT") is an orphan genetic peripheral polyneuropathy. Affecting approximately 1 in 2,500 individuals, this disease is the most common inherited disorder of the peripheral nervous system. Its onset typically occurs during the first or second decade of life, although it may be detected in infancy. Course of disease is chronic with gradual neuromuscular degeneration. The disease is invalidating with cases of accompanying neurological pain and extreme muscular disability. CMT is one of the best studied genetic pathologies with approximately 30,000 cases in France. While a majority of CMT patients harbour a duplication of a chromosome 17 fragment containing a myelin gene: PMP22 (form CMT1A), more than two dozens of genes have been implicated in different forms of CMT. Accordingly, although monogenic in origin, this pathology manifests clinical heterogeneity due to possible modulator genes. The genes mutated in CMT patients are clustering around tightly connected molecular pathways affecting differentiation of Schwann cells or neurons or changing interplay of these cells in peripheral nerves.

At present, the diagnostic of CMT disease is based on clinical criteria and electrophysiology data that distinguish only few subtypes of this disease. More precise classification relies on mutation's analysis in relevant genes if known.

The multiple mutations leading to CMT disease occur in more than 25 different genes. They are not identified for all cases of CMT disease and cannot be exhaustingly classified by genetic typing (Suter & Scherer, 2003; Berger et al., 2006; Niemann et al., 2006; Nave et al., 2007). Moreover, clinical heterogeneity does occur and not only is important for clinical characterization but provides further implication of specific management/treatment for functionally different forms (Sereda et al., 2003; Passage et al., 2004; Sahenk et al., 2005; Young et al., 2008).

For the moment, no drug treatment exists for this disease but some clinical management procedures have been described (Grandis & Shy, 2005; Kapur et al., 2007; Weiner et al., 2008) and clinical trials with ascorbic acid for the treatment of CMT1A form of this disease are under way (Burns et al., 2009).

The progression of this disease measured by CMT Neuropathy Score (CMTNS) is rather slow and necessitates long clinical trials with hundreds of patients.

The protein and RNA levels of PMP22 have been recently proposed as biological markers to follow up such trials pharmacodynamically as a substitute for CMTNS endpoint in a case of CMT1A (Li et al., 2005; Meyer zu Horste et al., 2007). Still, such analysis is tedious and requires invasive procedure. Moreover, expression of PMP22 in such biopsies is not correlated with severity of disease (Katona et al., 2009).

Patrocolo et al., 2009 reports elevated total cholesterol and triglycerides levels in a patient with Autosomal Dominant Hereditary Motor Sensory Neuropathy with Proximal Dominant Involvement (HMSN-P).

Yao et al., 1978 studies the distribution of specific fractions of cholesteryl esters in patients having hereditary neuropathies. This document provides no information regarding free cholesterol or LDL cholesterol levels.

Swartz et al., 1988 concerns immunogenicity of cholesterol and production of monoclonal IgM complement-fixing antibodies to cholesterol.

Niebroj-Dobosz et al., 1976 concerns patterns of different lipid fractions in neuropathic patients (such as total lipids, total phospholipids, free fatty acids or cholesterol esters). The authors conclude that there is no correlation between the type of lipid pattern changes and the clinical syndrome.

The availability of easily detectable biological markers would permit rapid diagnosis of functionally relevant forms of CMT and related diseases, clinical testing of efficacy of new medications and monitoring the individual response of patients to drug treatment and disease management.

SUMMARY OF INVENTION

The purpose of the present invention is to provide novel methods for detecting predisposition to, or diagnosis and/or prognosis of CMT disease and related disorders, as well as for assessing the responsiveness to the treatments and/or the efficacy of treatments in subjects having CMT or a related disorder.

As indicated herein, the present invention provides a method for the diagnosis of CMT and CMT related diseases. The present invention also provides methods for aiding in the diagnosis and sub-classification of neurological disorders, or in patient stratification step in clinical trials, including CMT and CMT related diseases, by quantifying the amount of lipids, amino acids, steroid hormones, carbohydrates, metals, arachidonic acid metabolites, biogenic amines, nucleosides, nucleotides, small peptides and proteins in a biological fluid sample of the subject, such as a cerebrospinal fluid, serum, saliva, urine, etc. and comparing the measured amount with a reference value for the biomarker. These methods can also be applied to quantification of biomarkers in extracts of biopsies including skin biopsy. The information thus obtained may be used to aid in the diagnosis, to diagnose the disease, or to predict potential drug response in the individual. The biomarkers are differentially present in subjects having a neurological disease, including CMT and CMT related diseases, versus subjects free of the disease.

One embodiment of the present invention is a method of diagnosing or assessing the likelihood that a patient is afflicted with a neurological disease, including CMT, preferably CMT1A, and CMT related diseases, the method comprising measuring a level of complex combination biomarkers of the present invention.

The present invention more specifically relates to an in vitro method for detecting the presence or risk of CMT disease in a mammal, or for aiding in the diagnosis, prognosis or sub-classification of CMT disease, or in patient stratification step in clinical trials, the method comprising determining the (relative) amount or the presence, absence or alteration of a target biomarker in a fluid biological sample from the subject, wherein said amount or alteration is indicative of the presence, risk, progression or severity of said disease, and wherein said biomarker is selected from lipids, amino acids, steroid hormones, metals, metabolites of arachidonic acid, biogenic amines, carbohydrates, peptides, nucleosides and nucleotides.

The present invention also relates to an in vitro method for assessing efficacy of a treatment against CMT in a mammal, the method comprising determining in a fluid biological sample from the subject, during the treatment, the (relative) amount or the presence, absence or alteration of a target biomarker selected from lipids, amino acids, steroid hormones, metals, metabolites of arachidonic acid, biogenic amines, carbohydrates, peptides, nucleosides and nucleotides, and comparing said amount or alteration to a level of said biomarker determined before treatment or at an earlier stage of treatment in said mammal, wherein a deviation is indicative of the efficacy of the treatment.

The methods of the invention may use one or more target biomarker(s). In a preferred embodiment, said target biomarker(s) are selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin, or combinations thereof.

In another embodiment, said one or more biomarkers are used in conjunction with at least one additional diagnostic test or marker for CMT, selected preferably from nucleic acids, proteinous, physiological, neurophysiological, genetic, behavioral, electrophysiological, clinical and phenotypical test or marker.

The present invention also relates to a use of one or more biomarker(s) of the present invention in a method of detecting predisposition to or diagnosis and/or prognosis of CMT disease in a mammalian subject.

DETAILED DESCRIPTION OF THE INVENTION

The present invention provides new diagnostic methods and tools for CMT and related disorders.

Within the context of this invention, CMT includes CMT1A, CMT1B, CMT1C, CMT1D, CMT1X, CMT2A, CMT2B, CMT2D, CMT2E CMT2F, CMT2I, CMT2J, CMT2-P0, CMT2K, CMT4A, CMT4B1, CMT4B2, CMT4C, CMT4D, CMT4F, CMT4, AR-CMT2A, CMT4J or other forms of Charcot-Marie-Tooth disease. In the most preferred embodiment, CMT is CMT1A.

Within the context of the present invention, the term "CMT related disorder" designates other diseases associated with neurological symptoms. The term "CMT related disorder" more particularly includes Alzheimer's disease (AD), senile dementia of AD type (SDAT), Parkinson's disease, Lewis body dementia, vascular dementia, autism, mild cognitive impairment (MCI), age-associated memory impairment (AAMI) and problem associated with ageing, post-encephalitic Parkinsonism, schizophrenia, depression, bipolar disease and other mood disorders, Huntington's disease, motor neurone diseases including amyotrophic lateral sclerosis (ALS), multiple sclerosis, idiopathic neuropathies, diabetic neuropathy, toxic neuropathies including neuropathy induced by drug treatments, neuropathies provoked by HIV, radiation, heavy metals and vitamin deficiency states, prion-based neurodegeneration, including Creutzfeld-Jakob disease (CJD), bovine spongiform encephalopathy (BSE), GSS, FFI, Kuru and Alper's syndrome.

The purpose of the present invention is to provide new body fluid biomarkers for diagnosing or monitoring CMT and related disorders, and for assessing the responsiveness of subjects or the efficacy of therapeutic treatments in subjects having CMT or a related disorder. Thus, according to a preferred embodiment, the method of the invention comprises the detection of the presence or absence or (relative) quantity of metabolites in body fluids.

An object of the invention resides in detecting (in vitro or ex vivo) the presence of or risk of developing CMT or a related disorder in a mammal, comprising the determination of the presence, in a biological sample of the mammal of an alteration in one or more selected body fluid biomarkers.

Another object of the invention resides in a method for detecting (in vitro or ex vivo) the presence of or risk of developing CMT or a related disorder in a mammal, comprising the determination of the presence, in a biological sample of the mammal, of an alteration of the level in one or more markers, the presence of such an alteration being indicative of the presence of or risk of developing CMT in said mammal.

In a preferred embodiment, a method of the invention is an in vitro method for detecting the presence or risk of CMT disease in a mammal, or for aiding in the diagnosis, prognosis or sub-classification of CMT disease, or aiding in patient stratification step in clinical trials, the method comprising determining the (relative) amount or the presence, absence or alteration of a target biomarker in a fluid biological sample from the subject, wherein said amount or alteration is indicative of the presence, risk, progression or severity of said disease, and wherein said biomarker is selected from lipids, amino acids, steroid hormones, metals, metabolites of arachidonic acid, biogenic amines, carbohydrates, peptides, nucleosides and nucleotides.

Within the context of the present invention, the term "alteration" of a target biomarker may designate an increase or a decrease of the target biomarker quantity in a fluid biological sample from the subject, in comparison with a control sample or reference value. Typically, the term "decrease" in relation to a biomarker level, designates a reduction of the concentration or level of the biomarker in a biological sample from the subject of at least 5% or 10% or 15% in comparison with a control sample or reference or mean value. Decreases may be more substantial, such as a reduction by at least 20% or 30% or 40% or even more. Similarly, the term "increase" in relation to the biomarker level, designates an augmentation of the concentration or level of the biomarker in a biological sample from the subject of at least 5% or 10% or 15% in comparison with a control sample or reference or mean value. Increases may be more substantial, such as increases by at least 20% or 30% or 40%, or even more.

Preferred types of alterations are disclosed below for each biomarker in Table A. This table indicates, for each biomarker, whether an increase or a decrease is indicative of CMT in human subjects. A distinction between male and females patients is also provided.

TABLE A

Increase (+) or decrease (−) of a biomarker concentration in CMT patients

| | total | female | male |
|---|---|---|---|
| Adrenaline | | | − |
| Alanine | − | − | |
| Alpha Amino Butyric acid | | | − |
| Citrulline | | − | |
| Cystine | − | | |
| Dopamine | + | | |
| Free cholesterol | − | − | − |
| Glutamine | − | − | |
| Hydroxyproline | − | − | |
| Iron | + | | |
| LDL cholesterol | | − | |
| LTB4 | | − | |
| Lysine | | − | |
| Methionine | | | + |
| Proline | | | + |
| Serotonin | + | | |
| T4 | − | | − |
| Testosterone | | | + |
| Threonine | − | | |
| Tryptophan | + | | + |
| Tyrosine | | − | |

Specific examples of alterations of each target biomarker(s) according to the invention are shown in Tables 1-4 of the experimental part.

Another embodiment of the present invention comprises qualifying and sub-classifying a CMT disease, for example CMT1A, CMT1B, CMT1C, CMT1D, CMT1X, CMT2A, CMT2B, CMT2D, CMT2E CMT2F, CMT2I, CMT2J, CMT2-P0, CMT2K, CMT4A, CMT4B1, CMT4B2, CMT4C, CMT4D, CMT4F, CMT4, AR-CMT2A, CMT4J or other forms of Charcot-Marie-Tooth disease or CMT related disorders in a subject, comprising measuring sets of complex biomarkers of the present invention.

In other aspects, methods of the present invention further comprise the step of managing the individual treatment. For example, if measurement of the set of biomarkers correlates with the presence of clinical sub-type CMT disease, then managing treatment comprises administering a matched drug or drug combination to slow or revert the progression of the disease. Further measurements can be compared to the previous measurements, or the standard to monitor the progression of the disease.

In another aspect of the invention, the method further comprises measuring the biomarker after treatment has begun, to monitor the progression of the disease.

In another embodiment, the method of the present invention comprises monitoring the progression of a CMT, preferably CMT1A, and measuring a level of sets of biomarkers of the present invention.

Another object of the invention relates to a method to evaluate or follow the response to a treatment for CMT in a subject, the method comprising a step of measuring the level of one or more markers, the presence of such an alteration before and/or during the treatment, and a comparison of the level thus measured with that measured at a former stage of the treatment or before treatment.

Another object of the invention relates to a method to evaluate or follow the response to a treatment of CMT in a subject, the method comprising a step of measuring the amount of one or more selected body fluid biomarkers before and/or during the treatment, and a comparison of the amount thus measured with that measured at a former stage of the treatment or before treatment.

The level of the biomarker(s), measured according to the method of the present invention, is correlated with neurological disease, preferably CMT disease. In preferred embodiments, this may be accomplished by comparing the measured amount to a reference value for the biomarker(s). The reference value can be obtained by measuring an amount of the biomarker(s) in age-matched control subjects that are not affected by the disease, or that are free of the disease.

Another object of the invention relates to an in vitro method for assessing efficacy of a treatment against CMT in a mammal, the method comprising determining in a fluid biological sample from the subject, during the treatment, the (relative) amount or the presence, absence or alteration of a target biomarker selected from lipids, amino acids, steroid hormones, metals, metabolites of arachidonic acid, biogenic amines, carbohydrates, peptides, nucleosides and nucleotides, and comparing said amount or alteration to a level of said biomarker determined before treatment or at an earlier stage of treatment in said mammal, wherein a deviation is indicative of the efficacy of the treatment.

Another embodiment of the present invention comprises monitoring the efficacy of a treatment method of a CMT, comprising measuring a level of complex set of biomarkers of the present invention. In embodiments, the efficacy of treatment is measured by monitoring levels of the biomarker in the subject compared to a reference, and/or compared to other previous tests of the subject or to an earlier stage of treatment/disease in the subject.

Another object of the invention relates to an improvement in methods of treating CMT or related disorders, the improvement consisting in measuring the level of expression of one or, preferably, several biomarkers before and/or during the treatment. The measurement of the level of biomarker expression, makes it possible to adapt the treatment according to the evolution of pathology and/or efficacy of the treatment.

In a preferred embodiment, diagnosing or monitoring CMT and related disorders, comprises the determination of the quantity (or of the presence or of the absence), in a biological sample of the mammal, of said body fluid biomarker(s) selected from lipids, amino acids, steroid hormones, carbohydrates, metals, metabolites of arachidonic acid, biogenic amines, nucleosides and nucleotides, small peptides and proteins.

In a preferred embodiment, the method of the invention comprises the determination of the quantity (or of the presence or of the absence), in a biological fluid sample of the mammal, of one or more body fluid biomarkers, wherein said body fluid biomarkers are selected from:
 lipids, preferably cholesterol and its metabolites, including dehydroepiandrosterone (DHEA), and including more preferably free cholesterol or LDL cholesterol, or their amount in regard of total cholesterol,
 amino acids or their derivatives, preferably including alanine, a amino butyric acid, citrulline, cystine, glutamine, hydroxyproline, lysine, methionine, proline, threonine, tryptophan and tyrosine, and/or arginine, asparagines, aspartic acid, glutamic acid, glycine, histidine, 1-methyl histidine, isoleucine, leucine, ornithine, phenylalanine, serine, taurine and valine,
 steroid hormones and their precursors or derivatives, preferably including T3 and T4 thyroid hormones, testosterone, 5α-dihydroprogesterone, allopregnanolone and corticosterone,
 metals, preferably iron and zinc, metabolites of arachidonic acid, preferably including leukotrienes (e.g., LTB4/5), and prostaglandins PGE2, prostacyclins PGI2 and tromboxanesTXA2 and TXB2, biogenic amines, preferably including adrenaline, dopamine and serotonin, carbohydrates, preferably sorbitol, nucleotides, preferably 3'-5'-cyclic adenosine monophosphate (cAMP), and any combination thereof.

More preferably, said body fluid biomarkers are selected from:

lipids, preferably cholesterol and its metabolites, including free cholesterol or LDL cholesterol, or their amount in regard of total cholesterol, amino acids or their derivatives, preferably including alanine, a amino butyric acid, citrulline, cystine, glutamine, hydroxyproline, lysine, methionine, proline, threonine, tryptophan and tyrosine, steroid hormones, preferably including T4 thyroid hormone and testosterone, metals, preferably iron, metabolites of arachidonic acid, preferably including leukotrienes (e.g., LTB4/5), biogenic amines, preferably including adrenaline, dopamine and serotonin, and any combination thereof.

In another preferred embodiment, the method of the invention comprises the determination of the quantity (or of the presence or of the absence), in a biological fluid sample of the mammal, of one or more body fluid biomarkers, wherein said body fluid biomarkers are selected from:

cholesterol metabolites, preferably including an ester of cholesterol, 27-hydroxycholesterol, pregnenolone, pregnenolone sulfate, and dehydroepiandrosterone sulfate (DHEAS), steroid hormones and their precursors or derivatives, preferably including cortisol, cortisone, aldosterone, androstanediol, androstenedione, estradiol and estrone, metabolites of arachidonic acid, preferably including prostaglandins PGD2 and PGF2α, 12-Hydroxyeicosatetraenoic acid (12-HETE) and lipoxins (LXA4 and LXB4), inositol and its derivatives, preferably including inositol monophosphates, phosphatidylinositol 3-phosphate [PI3P] and phosphatidylinositol (3,5)-bi-phosphate [PI(4,5)P2], sphingolipids or phospholipids or their derivatives, preferably including lysophosphatidic acid, phosphatidic acid and sphingosine-1-phosphate (S1P), endocannabinoids, preferably including arachidonoylethanolamine, 2-arachidonoyl glycerol, 2-arachidonyl glyceryl ether, N-arachidonoyl-dopamine and virodhamine, and any combinations thereof.

In another preferred embodiment, a method of the invention comprises determining in a fluid biological sample from the subject the (relative) amount or the presence, absence or alteration of a target biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin, as well as any combinations thereof.

In a preferred embodiment, the biomarker used in the invention is or comprises at least cholesterol, more preferably free cholesterol, and/or LDL cholesterol and/or their amount in regard of total cholesterol. Within the context of the present invention the term "LDL cholesterol" designates all forms of cholesterol contained in LDL, including non esterified cholesterol.

As shown in the experimental part, the inventors have surprisingly discovered that the level of free cholesterol or the level of LDL cholesterol decreases in diseased animals.

Thus, in the most preferred embodiment, the method of the invention comprises determining a decrease of free cholesterol and/or LDL cholesterol and/or their amount in regard of total cholesterol, in a fluid biological sample from the subject, wherein said decrease of free cholesterol and/or LDL cholesterol and/or their amount in regard of total cholesterol, is indicative of the presence, risk, progression or severity of the disease.

In a particular embodiment, the method of the invention comprises determining in a fluid biological sample from the subject, a decrease of the ratio of free cholesterol to total cholesterol.

In another particular embodiment, the method of the invention comprises determining a decrease of the ratio of LDL cholesterol to total cholesterol.

As indicated, the method may comprise the determination of several biomarkers, e.g., 2, 3, 4, 5 or even more. These may be determined simultaneously or sequentially in a fluid biological sample.

In a particular variant, the presence or the absence or the (relative) quantity of at least three biomarkers is determined simultaneously or sequentially in a fluid biological sample from the mammalian subject.

In another embodiment, the method of the invention comprises the determination of the presence or the absence or the (relative) quantity, in a biological sample of the mammal, of at least four distinct biomarkers.

In another embodiment, the sets of biomarkers used in methods of the invention are selected from Table 5.

In a preferred embodiment, the sets of biomarkers comprise:

free-cholesterol and alanine;

free-cholesterol and T4 and tryptophan and hydroxyproline;

free-cholesterol and hydroxyproline;

free-cholesterol and T4 and tryptophan;

free-cholesterol and T4 and serotonin;

free-cholesterol and T4 and hydroxyproline;

free-cholesterol and T4; or free-cholesterol and serotonin.

As illustrated in the examples, such sets of biomarkers are particularly efficient in predicting the presence of CMT disease. In particular, the results depicted in the examples show performances of 100% in training tests and between 78% and 100% in validation tests for these sets of biomarkers.

The level of said biomarker(s) may be determined by any methods known per se in the art, such as, without limitation, immunological methods, biochemical methods, chromatographic methods, enzymatic methods, cell based assays, in vitro tests, etc. Examples of suitable methods are disclosed in the experimental section. The level of biomarker(s) determined may be compared to a reference value, a control, or a mean value, wherein a deviation from said value is indicative of the presence, risk, progression or severity of CMT. The deviation should typically be superior to 5%, more preferably to 10%, even more preferably 15%.

Another aspect of the invention relates to a use of one or more biomarker(s) selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin in a method of detecting predisposition to or diagnosis and/or prognosis of CMT disease in a mammalian subject.

In a particular embodiment, the above biomarkers are used in a method of detecting predisposition to, diagnosis and/or prognosis of CMT disease, or aiding in patient stratification step in clinical trials, in conjunction with at least one additional diagnostic test or marker for CMT, selected preferably from proteinous, physiological, neurophysiological, genetic, behavioral, electrophysiological, clinical and phenotypical test or marker.

In another particular embodiment, the level of said biomarker(s) used in a method of detecting predisposition to or diagnosis and/or prognosis of CMT disease, or aiding in patient stratification step in clinical trials, is compared to a reference value wherein the deviation from said value is indicative of the presence, risk, progression or severity of CMT.

In particular embodiment, any of the above mentioned body fluid biomarkers, or their combinations, can be used in conjunction with at least one additional diagnostic test or marker for CMT, selected preferably from nucleic acids, proteinous, physiological, neurophysiological, genetic, behavioral, electrophysiological, clinical and phenotypical test or marker.

Said proteinous biomarkers, detectable in body fluids, which can be used for diagnostic of CMT or for monitoring of progression of CMT, or for monitoring of the efficacy of CMT-relevant drugs, include NEFH neurofilament, p75/LNGFR nerve growth factor receptor, NTRK3 receptor, SCIP transcription factor, cyclin D1, lysosomal-associated membrane protein LAMP1, ATG7 autophagy related 7 homolog, proteasome activator subunits PSME1/2, PSMA1 proteasome subunit, ITGB1/4 integrins, insulin-like growth factor 1 (IGF1), insulin-like growth factor binding proteins 1/2/5 (IGFBP1/2/5), vitronectin (VTN), tenascins (TNC/R/XB), SCN10A voltage-gated sodium channel, KCNC1 potassium voltage-gated channel, aldose reductases including AKR1B1, sorbitol dehydrogenase (SORD), inositol (myo)-1 (or 4)-monophosphatases IMPA1/2, ADP-ribosylation factor 6 (ARF6), calnexin (CANX), growth factors FGF2, PDGFA/B/C, VEGFA/B/C and TGFB1/2, neuregulins including NRG1, matrix metallopeptidase 2/9, tissue and urokinase plasminogen activators PLAT and PLAU, monocyte chemoattractant protein-1 (CCL2), leukemia inhibitory factor (LIF), interleukin 6, transferrin, and endogenous opioids POMC, PENK and PDYN as well as smaller peptides and other derivatives produced by metabolism of above mentioned molecules.

Additional protein biomarkers, useful for diagnostic of Charcot-Marie-Tooth disease (CMT) or for monitoring of progression of CMT, or for monitoring of efficacy of CMT-relevant drugs, can be selected from peripheral myelin protein 22 PMP22, from ciliary neurotrophic factor CNTF, fatty acid elongase ELOVl6, glypican GPC3, myosins MYO1B/1G, phosphoprotein enriched in astrocytes PEA15, calcium binding proteins S100A3/4, troponins TNNT1/3 and ferritin FTH1 as well as smaller peptides and other derivatives produced by their metabolism.

Further protein biomarkers, detectable in body fluids and useful for diagnostic of Charcot-Marie-Tooth disease or for monitoring of progression of CMT, or for monitoring of efficacy of CMT-relevant drugs, can be selected from proteins or smaller peptides and their derivatives encoded by ATP1A1, FGL2, ACAT2, ACTN2, AK1, ANK3, ANXA1, APOD, CD151, CD24A, CD9, CD99, CETN2, CHN1, CLIC4, COL1A1/2, COL2A1, COL3A1, COL4A1, CRYAB, CTSC, CYB5B, CYB561, DEAF1, EMID1, EPB4.1L2, EZR, FASN, FBLN2, FDFT1, FHL1, FOS, GAPD, GATM, HBA1, HBB, IGF2, ITIH5, KIT, LGALS1, LPL, LXN, MAPK3, MFGE8, MGLL, MMP12, MRAS, MSLN, MTAP1B, NECL1, NPR3, ODF2, OGN, OLFM1, PCOLCE, PMM1, PROS1, PYGM, RAB2, RAP1GDS1, SERPINE2, SH3GL3, SIRT2, SPP1, TPM1/2, TUBA2 and UCHL1 genes.

The above groups of genes (or the corresponding proteins or ligands) represent valuable biomarkers which may be used, alone or in various combinations, to diagnose CMT or related disorders.

In still another aspect, the present invention provides a kit comprising a solid support comprising at least one capture agent attached thereto, wherein the capture agent binds or reacts with one or more component(s) of the biomarker protein complex of the present invention.

In a preferred embodiment, the kit of the invention comprises a solid support comprising at least one capture agent attached thereto, wherein the capture agent binds or reacts with at least one biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin. In a preferred embodiment, the kit of the invention comprises at least one compound binding to or reacting with at least one biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin for the diagnostic, prognostic and/or for assessing the efficacy of a treatment or following the evolution of CMT1A disease.

The method of the invention is applicable to any biological sample of the mammal to be tested, in particular any sample comprising metabolites. Examples of such samples include blood, plasma, serum, saliva, urine, feces, tissue biopsy, etc. The sample can be obtained by any technique known per se in the art, for example by collection using e.g., non invasive techniques, or from collections or banks of samples, etc. The sample can in addition be pretreated to facilitate the accessibility of the target molecules, for example by lysis (mechanical, chemical, enzymatic, etc.), purification, centrifugation, separation, etc.

The invention is applicable to any mammal, preferably to a human.

Further aspects and advantages of this invention will be disclosed in the following experimental section, which shall be considered as illustrative only.

EXAMPLES

I. Identification of New Markers and Quantitation of Biomarkers

The invention discloses biomarkers of body fluids useful for the diagnostic, prognostic and/or for assessing the efficacy of a treatment or following the evolution of CMT disease.

I.1 CMT1A Transgenic Rat Model and Serum Samples Collection

The CMT transgenic rat model is a hemizygous PMP22 transgenic rat bearing three additional copies of mouse PMP22 gene show signs of demyelination in peripheral and cranial nerves (Sereda et al., 1996; Grandis et al., 2004).

This CMT rat model is a good approximation of human CMT1A disease from a clinical point of view. Furthermore, the CMT rats already served as a model for an experimental CMT1A therapy (Meyer zu Horste et al., 2007).

Inventors have looked for small molecules showing differential levels in wild type and transgenic rats thus constituting relevant biomarkers for CMT disease.

Except otherwise specified, CMT1A model rats, four months old, are anaesthetized with Ketamine (Imalgene) 100 mg/kg, ip. Blood is collected by cardiac puncture in two different tubes:

in one sterilized blood collection tube for coagulation; serum is collected and stored at −80° C.

in one EDTA RNAse free tube; after centrifugation (+4° C.; 1260 g; 10 min), plasma is stored at −80° C.

I.2 Quantitation Methods

Free Cholesterol

Cholesterol was firstly extracted from samples with heptanes. Free cholesterol was further analyzed using a method adapted from Dong et al. (2007): cholest-4-en-3,6-dione formed from the oxidation of non-esterified cholesterol by the Jones oxidation was measured by HPLC/UV analyses. Stigmasterol was used as an internal standard.

Sorbitol

Proteins are firstly precipitated with ethanol. Sorbitol is analyzed mainly according the Dionex N° 20 technical note, using anion exchange chromatography coupled with electrochemical detector.

Metals

Quantitation of Iron and Zinc was performed by ICP/MS after mineralization of serum samples.

Arachidonic Acid Metabolites

Enzyme ImmunoAssays (EIA) kits from Cayman chemical were used to analyze:
Prostaglandin $E_2$ (ref. 514010)
Leukotriene $B_4$ (ref. 520111)
Thromboxane $B_2$ (ref. 519031)
6-keto Prostaglandine $F_{1\alpha}$ (ref. 515211)

Cyclic Adenosine MonoPhosphate

After precipitation of plasma proteins with ethanol, cAMP is analyzed with an EIA kit from Cayman chemical (ref 581001) according the manufacturer instructions.

Catecholamines

A solid phase extraction (SPE) was performed to concentrate and purify the samples. Adrenaline, dopamine, and serotonin were further analyzed by ion pair chromatography.

Amino Acids

Plasma proteins were precipitated with sulfosalicylic acid prior to analyzes. Derivatized amino acids quantitation was performed with a spectrophotometer after an automated cation exchange chromatography process.

Thyroid Hormones

Prior to the precipitation of plasma proteins with methanol, an internal standard was added to samples. Triiothyronine (T3) and thyroxine (T4) were then quantified by an HPLC coupled to LC-MS/MS mainly according to Soukhova et al (2004).

Neurosteroids

CMT1A model rats, four months old, were decapitated and blood was collected in two different tubes:

in one sterilized blood collection tube for coagulation; serum was collected and stored at −80° C.

in one EDTA RNAse free tube; after centrifugation (+4° C.; 1260 g; 10 min), plasma was stored at −80° C.

Prior to analysis, plasma proteins were precipitated and neurosteroids were then purified and concentrated by SPE. Neurosteroids were further chemically derivatized with either 2-hydrozino-1-methylpyridine (to lower the detection threshold (Higashi et al., 2005) or picolinic acid (Yamashita et al., 2007). According to derivatization method, internal standard is $^2H$ testosterone or $^2H$ 3α-androstanediol. HPLC analysis of Neurosteroids was coupled to a mass spectrometer. Searched neurosteroids and derivatives were aldosterone, pregnelonone sulfate, allopregnanolone, progesterone, 5α-dihydroprogesterone (DHP), 3α-androstanediol, testosterone, 5α dihydrotestosterone, DHEA and corticosterone.

Estrogens

Blood is collected as above. As for neurosteroids, estrone and estradiol are extracted from sample with ethyl acetate prior to derivatization with picolinic acid purification and a concentration and purification step by SPE. $^2H$-estrone and $^2H$-17β-estradiol are used as internal standards.

I.3 Results

Duplicate samples were analyzed for each biomarker. Statistical analysis (student test, bilateral, type 3) comparing WT rats versus CMT1A (transgenic) rats was performed. Results are summarized in the three tables below. These tables report the mean level of biomarkers which present a notable difference (P<0.2) between WT and CMT1A rats in male and female (table 1), in only male (table 2) and in only female (table 3).

The analysis of biomarkers has revealed that plasmatic free cholesterol level is significantly decreased in CMT1A male (P=0.05) and female rats (P=0.06) compared to WT rats. In females, our results displayed a significant decrease of alpha-aminobutyric acid (P=0.019), glutamine (P=0.025) and tyrosine (P=0.03) plasmatic levels versus controls.

Our results also show a significant decrease of the following biomarkers: alanine, cystine, glutamine, hydroxyproline, threonine, T4 thyroid hormone, citrulline, LTB4, adrenaline, and lysine; and a significant increase of the following biomarkers: tryptophan, testosterone, dopamine, serotonin, iron, methionine, and proline (Table 1, 2 and 3).

I.4 Fluid Biological Samples Collection and Quantification Methods

Biomarkers of the invention can be easily quantified from other biological fluids. As an example quantitation from saliva sample are described by Karjalainen et al. (2007) for cholesterol, by Syrjänen et al. (1990) for glutamine and tyrosine. Likewise, those small molecules can be quantified in urine as described elsewhere for cholesterol (Cenedella et al., 1981) and for amino acids (Venta et al., 2001).

TABLE 1

| biomarkers | WT MEAN | s.e.m. | TG MEAN | s.e.m. | P |
| --- | --- | --- | --- | --- | --- |
| Free cholesterol (µg/ml) | 144.82 | 4.18 | 118.45 | 3.96 | 0.0004 |
| Alanine (µmol/l) | 659.67 | 44.19 | 523.50 | 46.31 | 0.059 |
| Cystine (µmol/l) | 15.50 | 2.85 | 8.67 | 2.51 | 0.103 |
| Glutamine (µmol/l) | 792.00 | 60.46 | 694.50 | 18.11 | 0.174 |
| Hydroxyproline (µmol/l) | 54.00 | 4.41 | 41.33 | 6.31 | 0.135 |
| Threonine (µmol/l) | 295.00 | 20.30 | 258.17 | 15.76 | 0.184 |
| Tryptophan (µmol/l) | 79.83 | 4.76 | 93.00 | 3.94 | 0.060 |
| Dopamine (ng/ml) | 0.30 | 0.02 | 0.41 | 0.07 | 0.195 |
| Serotonin (ng/ml) | 112.50 | 22.82 | 406.05 | 133.26 | 0.079 |
| T4 (ng/ml) | 52.57 | 4.26 | 42.64 | 3.11 | 0.092 |

TABLE 2

| | male | | | | |
|---|---|---|---|---|---|
| | WT | | TG | | |
| biomarkers | MEAN | s.e.m. | MEAN | s.e.m. | P |
| Free cholesterol (µg/ml) | 146.11 | 7.80 | 120.74 | 6.78 | 0.050 |
| Citrulline (µmol/l) | 109.00 | 9.29 | 92.00 | 3.61 | 0.201 |
| Methionine (µmol/l) | 49.67 | 2.73 | 55.67 | 1.76 | 0.150 |
| Proline (µmol/l) | 224.67 | 19.54 | 265.00 | 14.50 | 0.179 |
| Tryptophan (µmol/l) | 84.33 | 5.24 | 99.00 | 4.93 | 0.111 |
| Tyrosine (µmol/l) | 87.00 | 5.13 | 98.67 | 3.93 | 0.150 |
| Testosterone (ng/ml) | 1.81 | 0.40 | 3.37 | 0.85 | 0.201 |
| T4 (ng/ml) | 59.23 | 3.21 | 48.84 | 2.00 | 0.063 |
| Iron (µg/ml) | 4.77 | 0.45 | 7.03 | 1.24 | 0.134 |

TABLE 3

| | female | | | | |
|---|---|---|---|---|---|
| | WT | | TG | | |
| biomarkers | MEAN | s.e.m. | MEAN | s.e.m. | P |
| Free cholesterol (µg/ml) | 143.54 | 4.41 | 116.16 | 4.88 | 0.006 |
| LTB4 (pg/ml) | 421.46 | 43.75 | 335.67 | 26.36 | 0.184 |
| Alanine (µmol/l) | 660.33 | 46.83 | 551.33 | 44.86 | 0.168 |
| Alpha Amino Butyric acid (µmol/l) | 13.33 | 1.33 | 6.67 | 0.88 | 0.019 |
| Glutamine (µmol/l) | 905.33 | 46.94 | 687.33 | 38.84 | 0.025 |
| Hydroxyproline (µmol/l) | 49.00 | 6.66 | 29.00 | 2.52 | 0.081 |
| Lysine (µmol/l) | 510.67 | 25.96 | 419.00 | 22.50 | 0.057 |
| Tyrosine (µmol/l) | 80.00 | 2.65 | 56.33 | 5.36 | 0.030 |
| Adrenaline (ng/ml) | 7.99 | 0.76 | 5.97 | 0.58 | 0.107 |

II. Identification and Quantitation of Other Cholesterol Related Biomarkers

II.1 CMT1A Transgenic Rat Model and Serum Samples Collection

The CMT transgenic rat model and samples collection are the same as described above (see section I.1).

II.2 Cholesterol Quantitation Methods

Total Cholesterol

Total cholesterol has been determined by an enzymatic assay with ABX Pentra Cholesterol CP kit (Horiba). The cholesterol is consumed by cholesterol esterase and cholesterol oxidase in a color forming reaction where the color produced is proportional to the amount of the total cholesterol present in the sample.

LDL Cholesterol

LDL cholesterol has been determined by an enzymatic assay with ABX Pentra LDL Direct CP kit (Horiba). The method is in a two reagents format and depends on the properties of the used detergents. The first detergent solubilizes all the non LDL lipoprotein particles. The cholesterol released is consumed by cholesterol esterase and cholesterol oxidase in a non-color forming reaction. the second detergent solubilizes the remaining LDL particles and a chromogenic coupler allows for color formation. The enzyme reaction in the presence of the coupler produces color that is specifically proportional to the amount of LDL cholesterol present in the sample.

II.3 Results

Results presented in table 4 below were extracted from independent assays and analysed with a bilateral Student's t test comparing 20 WT rats versus 19 CMT1A (transgenic) rats.

TABLE 4

| | WT | | TG | | |
|---|---|---|---|---|---|
| Biomarkers | MEAN | s.e.m | MEAN | s.e.m | P |
| Total cholesterol | 1.81 | 0.07 | 1.77 | 0.05 | 0.66129 |
| LDL cholesterol | 0.26 | 0.02 | 0.21 | 0.01 | 0.03951 |

Our results show that LDL-cholesterol level is significantly decreased (P=0.039) in CMT1A rats (TG) compared to WT rats while total cholesterol level isn't significantly modified. LDL-cholesterol level is very easily quantifiable with commonly used detection kits.

Correlation of Biomarkers Concentration with Results from Behavioral Tests, Histology, Gene Expression and Electrophysiology Motor performance and muscular strength, Sensory Nerve Action Potentials (SNAP), axonal diameter distribution and myelin sheath of fixed sciatic nerve, fiber content in fixed muscles and pmp22 mRNA expression were compared with biomarkers amount measured in biological fluids. The test used is a test of linear association between paired samples using Pearson's product moment correlation. It is a unilateral test and a significance threshold of 0.05 is applied on p-values.

Such analysis demonstrates that the levels of the biomarkers of the invention are correlated with some of above mentioned behavioral tests, histology, PMP22 gene expression and electrophysiology confirming thereby the significance of those biomarkers in CMT1A physiology and the pertinence of the use of these biomarkers in the diagnostic and follow-up of CMT1A.

III. Identification of Disease Predictors from Biomarkers of the Invention

Statistical analysis of level of biomarkers of the invention obtained in above experiments shows that said biomarkers can also be used in different sets of grouped biomarkers to predict the presence of disease with a good score. Predictability scores are shown for some of possible sets comprising several of molecules identified herein as biomarkers for CMT disease (table 5).

Briefly, diagnostic of the disease was performed by applying a Linear-Discriminant-Analysis (LDA), commonly used in statistics, pattern recognition and machine learning to find a linear combination of features which characterize or separate two or more classes of objects. The LDA was implemented in R (http://www.r-project.org/).

The LDA algorithm was applied on several set of biomarkers selected on the basis of their correlation to the trait of interest (here transgenic versus wild-type). In order to properly assess the performances of each set of biomarkers, groups of rats were split into independent "training set" (75% of rats) on which LDA was trained, and a "validation set" (25% of rats), on which the trained algorithm was validated. To be homogeneous, training and validation sets were made of equal proportions of transgenic/wild-type and male/female rats. Since the level of biomarkers differs between males and females, for a given set of biomarkers, LDA was trained and validated separately on males and females. Finally the trained LDA was used to classify each rat of the training and validation sets into "wild-type" and "transgenic", and the proportion of rats that were well-classified allowed assessing the performances of the algorithm. This procedure was reapplied iteratively in order to average the performances over all the possible samplings.

TABLE 5

| Biomarkers | Training | | | Validation | | |
| --- | --- | --- | --- | --- | --- | --- |
| | Male | Female | Male and Female | Male | Female | Male and Female |
| Hydroxyproline and Alanine | 68% | 100% | 84% | 45% | 83% | 64% |
| Tryptophan and Hydroxyproline | 86% | 100% | 93% | 56% | 84% | 70% |
| T4 and Tryptophan and Hydroxyproline and Alanine | 92% | 100% | 96% | 60% | 89% | 75% |
| T4 and Hydroxyproline | 92% | 100% | 96% | 60% | 79% | 69% |
| T4 and Hydroxyproline and Alanine | 92% | 100% | 96% | 61% | 83% | 72% |
| Hydroxyproline and Serotonin and Alanine | 81% | 100% | 90% | 61% | 84% | 72% |
| Hydroxyproline and Serotonin | 74% | 100% | 87% | 61% | 72% | 67% |
| T4 and Tryptophan and Hydroxyproline | 94% | 100% | 97% | 61% | 89% | 75% |
| Tryptophan and Hydroxyproline and Alanine | 89% | 100% | 94% | 61% | 73% | 67% |
| Total of 20 biomarkers* | 100% | 100% | 100% | 62% | 72% | 67% |
| T4 and Tryptophan and Hydroxyproline and Serotonin | 95% | 100% | 97% | 67% | 77% | 72% |
| Tryptophan and Hydroxyproline and Serotonin and Alanine | 86% | 100% | 93% | 67% | 72% | 69% |
| T4 and Serotonin | 95% | 74% | 84% | 71% | 62% | 67% |
| Tryptophan and Hydroxyproline and Serotonin | 89% | 100% | 95% | 72% | 72% | 72% |
| T4 and Tryptophan and Serotonin and Alanine | 92% | 95% | 93% | 72% | 77% | 75% |
| T4 and Tryptophan | 95% | 97% | 96% | 72% | 77% | 75% |
| T4 and Hydroxyproline and Serotonin and Alanine | 85% | 95% | 90% | 72% | 83% | 78% |
| T4 and Tryptophan and Alanine | 94% | 97% | 96% | 72% | 78% | 75% |
| T4 and Hydroxyproline and Serotonin | 91% | 100% | 96% | 73% | 71% | 72% |
| T4 and Alanine | 89% | 83% | 86% | 73% | 73% | 73% |
| T4 and Tryptophan and Hydroxyproline and Serotonin and Alanine | 94% | 100% | 97% | 73% | 83% | 78% |
| Serotonin and Alanine | 78% | 78% | 78% | 73% | 71% | 72% |
| T4 and Serotonin and Alanine | 86% | 78% | 82% | 73% | 71% | 72% |
| T4 and Tryptophan and Serotonin | 94% | 97% | 96% | 73% | 77% | 75% |
| Tryptophan and Alanine | 92% | 83% | 87% | 77% | 61% | 69% |
| Free-cholesterol and Hydroxyproline and Serotonin and Alanine | 100% | 100% | 100% | 78% | 78% | 78% |
| Free-cholesterol and Tryptophan and Hydroxyproline and Alanine | 100% | 100% | 100% | 78% | 84% | 81% |
| Free-cholesterol and Tryptophan and Hydroxyproline and Serotonin and Alanine | 100% | 100% | 100% | 78% | 72% | 75% |
| Free-cholesterol and Hydroxyproline and Alanine | 100% | 100% | 100% | 78% | 88% | 83% |
| Tryptophan and Serotonin | 86% | 82% | 84% | 78% | 66% | 72% |
| Free-cholesterol and Tryptophan and Hydroxyproline | 100% | 100% | 100% | 83% | 83% | 83% |
| Free-cholesterol and Tryptophan and Alanine | 100% | 100% | 100% | 84% | 72% | 78% |
| Tryptophan and Serotonin and Alanine | 83% | 84% | 83% | 84% | 72% | 78% |
| Free-cholesterol and Tryptophan and Serotonin and Alanine | 100% | 100% | 100% | 84% | 72% | 78% |
| Free-cholesterol and Hydroxyproline and Serotonin | 100% | 100% | 100% | 84% | 77% | 80% |
| Free-cholesterol and Tryptophan and Hydroxyproline and Serotonin | 100% | 100% | 100% | 84% | 73% | 79% |
| Free-cholesterol and Serotonin and Alanine | 100% | 100% | 100% | 84% | 79% | 81% |
| Free-cholesterol and T4 and Serotonin and Alanine | 100% | 100% | 100% | 88% | 78% | 83% |
| Free-cholesterol and T4 and Tryptophan and Alanine | 100% | 100% | 100% | 89% | 88% | 88% |
| Free-cholesterol and T4 and Hydroxyproline and Alanine | 100% | 100% | 100% | 89% | 90% | 89% |
| Free-cholesterol and T4 and Tryptophan and Serotonin and Alanine | 100% | 100% | 100% | 89% | 77% | 83% |
| Free-cholesterol and T4 and Tryptophan and Hydroxyproline and Serotonin and Alanine | 100% | 100% | 100% | 89% | 78% | 84% |
| Free-cholesterol and T4 and Tryptophan and Hydroxyproline and Alanine | 100% | 100% | 100% | 89% | 88% | 89% |
| Free-cholesterol and T4 and Hydroxyproline and Serotonin and Alanine | 100% | 100% | 100% | 89% | 78% | 84% |
| Free-cholesterol and T4 and Tryptophan and Hydroxyproline | 100% | 100% | 100% | 94% | 94% | 94% |
| Free-cholesterol and T4 and Hydroxyproline and Serotonin | 100% | 100% | 100% | 94% | 77% | 86% |

TABLE 5-continued

| Biomarkers | Training | | | Validation | | |
|---|---|---|---|---|---|---|
| | Male | Female | Male and Female | Male | Female | Male and Female |
| Free-cholesterol and T4 and Tryptophan and Serotonin | 100% | 100% | 100% | 94% | 79% | 87% |
| Free-cholesterol and T4 and Alanine | 100% | 100% | 100% | 94% | 83% | 89% |
| Free-cholesterol and T4 and Tryptophan and Hydroxyproline and Serotonin | 100% | 100% | 100% | 94% | 77% | 86% |
| Free-cholesterol and Hydroxyproline | 100% | 100% | 100% | 94% | 94% | 94% |
| Free-cholesterol and Tryptophan and Serotonin | 100% | 100% | 100% | 95% | 67% | 81% |
| Free-cholesterol and Alanine | 100% | 100% | 100% | 95% | 89% | 92% |
| Free-cholesterol and T4 and Tryptophan | 100% | 100% | 100% | 95% | 89% | 92% |
| Free-cholesterol and Tryptophan | 100% | 100% | 100% | 95% | 78% | 86% |
| Free-cholesterol and T4 and Serotonin | 100% | 100% | 100% | 100% | 78% | 89% |
| Free-cholesterol and Serotonin | 100% | 100% | 100% | 100% | 79% | 89% |
| Free-cholesterol and T4 and Hydroxyproline | 100% | 100% | 100% | 100% | 95% | 97% |
| Free-cholesterol and T4 | 100% | 100% | 100% | 100% | 95% | 97% |

*Total of 20 biomarkers: Free Cholesterol, T4, Tryptophan, Hydroxyproline, Serotonin, Alanine, alpha-AminoButyricAcid, Citrulline, Cystine, Glutamine, Lysine, Methionine, Proline, Threonine, Tyrosine, Testosterone, Iron, LTB4, Adrenaline, Dopamine.

BIBLIOGRAPHY

Berger P. et al. Schwann cells and the pathogenesis of inherited motor and sensory neuropathies (Charcot-Marie-Tooth disease). Glia. 2006; 54(4):243-257.

Burns J. et al. Ascorbic acid for Charcot-Marie-Tooth disease type 1A in children: a randomised, double-blind, placebo-controlled, safety and efficacy trial. Lancet Neurol. 2009; 8(6):537-544.

Cenedella R. J. et al. Studies on the source of urinary cholesterol in the normal human male. The Journal of Lipid Research. 1981; 22:122-130.

Dong J. et al. Jones oxidation and high performance liquid chromatographic analysis of cholesterol in biological samples J. Chromatogr. B (2007); 858:239-246.

Grandis M. et al. Early abnormalities in sciatic nerve function and structure in a rat model of Charcot-Marie-Tooth type 1A disease. Exp Neurol. (2004); 190(1):213-23.

Grandis M & Shy M E. Current Therapy for Charcot-Marie-Tooth Disease. Curr Treat Options Neurol. 2005; 7(1):23-31.

Higashi T. et al. 2-Hydrazino-1-methylpyridine: a highly sensitive derivatization reagent for oxosteroids in liquid chromatography-electrospray ionization-mass spectrometry. samples J. Chromatogr. B (2005); 825:214-222.

Kapur S. et al. Anesthetic management of a parturient with neurofibromatosis 1 and Charcot-Marie-Tooth disease. J Clin Anesth. 2007; 19(5):405-406.

Karjalainen S. et al. Salivary cholesterol of healthy adults in relation to serum cholesterol concentration and oral health. J Dent Res. 1997; 76(10):1637-1643.

Katona I. et al. PMP22 expression in dermal nerve myelin from patients with CMT1A. Brain. 2009; 132(Pt 7):1734-1740.

Li J. et al. Skin biopsies in myelin-related neuropathies: bringing molecular pathology to the bedside. Brain. 2005; 128(Pt 5):1168-1177.

Meyer zu Horste G et al. Antiprogesterone therapy uncouples axonal loss from demyelination in a transgenic rat model of CMT1A neuropathy. Ann. Neurol. (2007); 61(1):61-72.

Nave K A. et al., Mechanisms of disease: inherited demyelinating neuropathies. Nat Clin Pract Neurol. 2007; 3(8): 453-464.

Niebrój-Dobosz I. et al. Serum lipids in various polyneuropathies. Neurol Neurochir Pol. 197711(4):421-426

Niemann A. et al. Pathomechanisms of mutant proteins in Charcot-Marie-Tooth disease. Neuromolecular Med. 2006; 8(1-2):217-242.

Passage E. et al. Ascorbic acid treatment corrects the phenotype of a mouse model of CMT disease. Nature Med. 2004; 10(4): 396-401.

Patroclo C B. et al. Autosomal dominant HMSN with proximal involvement: new Brazilian cases. Arquivos de Neuro-Psiquiatria. 2008; 67(3B):892-896

Sahenk Z. et al. NT-3 promotes nerve regeneration and sensory improvement in CMT1A mouse models and in patients. Neurology. 2005; 65(5):681-689.

Sereda M. et al. A transgenic rat model of Charcot-Marie-Tooth disease. Neuron. (1996); 16(5):1049-60.

Sereda M W. et al. Therapeutic administration of progesterone antagonist in a model of Charcot-Marie-Tooth disease (CMT-1A). Nat Med 2003; 9: 1533-1537.

Suter U & Scherer S S. Disease mechanisms in inherited neuropathies. Nat. Rev. Neurosci. 2003; 4: 714-726.

Soukhova N. et al. Isotope dilution tandem mass spectrometric method for T4/T3. Clin Chim Acta. (2004); 343 (1-2):185-90.

Syrjänen S M. et al. Free amino acid levels in oral fluids of normal subjects and patients with periodontal disease. Arch Oral Biol. 1990; 35(3):189-193.

Venta R. et al. Year-Long Validation Study and Reference Values for Urinary Amino Acids Using a Reversed-Phase HPLC Method. Clinical Chemistry. 2001; 47: 575-583

Weiner D S. et al. The Akron dome midfoot osteotomy as a salvage procedure for the treatment of rigid pes cavus: a retrospective review. J Pediatr Orthop. 2008; 28(1):68-80.

Yamashita K. et al. Highly sensitive determination of estrone and estradiol in human serum by liquid chromatography-electrospray ionization tandem mass spectrometry. Steroids (2007); 72:819-827.

Yao J K. et al. Lipid abnormalities in hereditary neuropathy: Part 2. Serum phospholipids. Journal of the Neurological Sciences. 1978; 36(2):225-236.

Young P. et al. Treatment for Charcot-Marie-Tooth disease. Cochrane Database Syst Rev. 2008; (1): CD006052.

The invention claimed is:

1. A method of detecting and treating a presence or risk of Charcot-Marie-Tooth type 1A disease in a mammal, the method comprising:
   (i) obtaining a plasma or serum sample from the mammal,
   (ii) extracting cholesterol from said plasma or serum sample with heptanes,
   (iii) oxidizing the extracted cholesterol by a Jones oxidation, wherein free cholesterol is oxidized into cholest-4-en-3,6-dione,
   (iv) quantifying the amount of cholest-4-en-3,6-dione by HPLC/UV analysis which corresponds to the plasma or serum amount of free cholesterol,
   (v) comparing said amount of free cholesterol with an age-matched plasma or serum control sample or reference value,
   (vi) detecting the presence or risk of Charcot-Marie-Tooth type 1A disease in said mammal if said amount of free cholesterol is reduced as compared to the control sample or value of step (v), and
   (vii) treating the mammal identified as having or being at risk of having Charcot-Marie-Tooth type 1A disease according to step (vi) by administering a drug or drug combination that treats Charcot-Marie-Tooth type 1A disease.

2. The method of claim 1, wherein the amount of total cholesterol is measured.

3. The method of claim 1, further comprising:
   (a) simultaneously or sequentially quantifying the amount of at least one second biomarker from a fluid biological sample from said mammal, wherein said at least one second biomarker is selected from the group consisting of low-density lipoprotein cholesterol, alanine, α-aminobutyric acid, citrulline, cystine, glutamine, hydroxyproline, lysine, methionine, proline, threonine, tryptophan, tyrosine, thyroxine (T4), testosterone, iron, leukotriene B4, adrenaline, dopamine and serotonin; and
   (b) comparing the value obtained in (a) with a reference or control value from the mammal.

4. The method of claim 3, wherein said at least one second biomarker is:
   alanine;
   thyroxine, tryptophan and hydroxyproline;
   hydroxyproline;
   thyroxine and tryptophan;
   thyroxine and serotonin;
   thyroxine and hydroxyproline;
   thyroxine; or
   serotonin.

5. The method of claim 1, wherein at least one additional diagnostic test for Charcot-Marie-Tooth type 1A disease is performed, wherein said additional diagnostic test is selected from the group consisting of detection of a nucleic acid marker, detection of a proteinous marker, a physiological test, a neurophysiological test, a genetic test, a behavioral test, an electrophysiological test, a clinical test, and a phenotypical test.

* * * * *

UNITED STATES PATENT AND TRADEMARK OFFICE
CERTIFICATE OF CORRECTION

PATENT NO.        : 9,494,605 B2                                              Page 1 of 1
APPLICATION NO.   : 13/510700
DATED             : November 15, 2016
INVENTOR(S)       : Cohen et al.

It is certified that error appears in the above-identified patent and that said Letters Patent is hereby corrected as shown below:

In the Specification

Column 7,
Line 16, "a amino" should read --α amino--.

Signed and Sealed this
Eleventh Day of April, 2017

Michelle K. Lee
*Director of the United States Patent and Trademark Office*